US005723653A

United States Patent [19]
Santhanam

[11] Patent Number: 5,723,653
[45] Date of Patent: *Mar. 3, 1998

[54] LIQUID RHEOLOGICAL ADDITIVES PROVIDING RHEOLOGICAL PROPERTIES TO NON-AQUEOUS SYSTEMS

[75] Inventor: Mahalingam Santhanam, E. Windsor, N.J.

[73] Assignee: Rheox, Inc., Hightstown, N.J.

[*] Notice: The term of this patent shall not extend beyond the expiration date of Pat. No. 5,510,452.

[21] Appl. No.: 761,870

[22] Filed: Dec. 9, 1996

[51] Int. Cl.$^6$ ............................................. C07C 69/34
[52] U.S. Cl. ............................................. 560/196; 524/186
[58] Field of Search ............................... 528/291, 295, 528/3; 560/196; 525/437, 438, 451; 524/186

[56] References Cited

U.S. PATENT DOCUMENTS

| | | | |
|---|---|---|---|
| 5,284,496 | 2/1994 | Baillargeon et al. | 44/393 |
| 5,510,452 | 4/1996 | Santhanam | 528/291 |

*Primary Examiner*—Melvyn I. Marquis
*Assistant Examiner*—D. Aylward
*Attorney, Agent, or Firm*—Michael J. Cronin

[57] ABSTRACT

A liquid, pourable 100% active rheological additive especially useful for thickening organic compositions which in one aspect comprises an active hydrogen containing compound such as a polyol, one or more polycarboxylic acids or isocynanates, and a functional chain ending unit. The additive, which exists in a pourable, pumpable form at up to a 100% as a rheologically active composition, exhibits excellent thickening efficiency for systems including inks, epoxies, polyesters, paints, greases and other systems, including ease of dispersibility, without adversely affecting gloss. The additive may operate by both an associative and a reaction mechanism to provide rheological viscosity properties to such systems, and is also similarly useful for aqueous systems.

13 Claims, No Drawings

LIQUID RHEOLOGICAL ADDITIVES PROVIDING RHEOLOGICAL PROPERTIES TO NON-AQUEOUS SYSTEMS

FIELD OF THE INVENTION

The present invention is directed to an improved rheological additive for organic systems which is in a liquid form, is free of any solvent, and is pourable at ambient temperatures. Such an additive imparts improved rheological activity to many types of organic systems, including paints, coatings, sealants, inks and varnishes. The present invention is also directed to organic compositions and systems containing such additives.

BACKGROUND OF THE INVENTION

Paint and coating manufacturers have long sought additives, generally referred to as thickeners, thixotropes, rheological additives, or rheological control agents, which are used to modify the rheological properties of various liquid organic compositions. The same desire has been felt by manufacturers of inks, epoxies, polyesters and greases.

Additives have long been used in coating compositions for various purposes. Thus, viscosity control agents, storage-stability agents, anti-settling agents, sag-control agents, and other materials are added to organic coating compositions in minor amounts for their respective functions. Rheology additives or modifiers (also called thickeners, rheological control agents and thixotropes) are added to such compositions not only to alter the viscosity of the coating composition, but also to maintain the viscosity at desired levels under varying process conditions and end-use situations. Other effects obtained from rheology modifiers include improvement in pigment suspension, leveling and flow. Some of these properties are also desired in other types of compositions, for instance, oil well drilling fluids.

To be effective, especially for paints and coatings, such rheological control agents must provide proper viscosity and thixotropic control characteristics to the systems in which they are employed. Organophilic clays have been shown to be useful to thicken various organic and solvent-based compositions. Among numerous United States patents owned by Rheox, Inc., the assignee of this invention, several describe various kinds of organically—modified clays as rheological additives—see U.S. Pat. Nos. 4,208,218; 4,412,018; 4,517,112; 4,695,402; and 5,075,033. Fumed silica and precipitated silica have also been used to thicken certain types of organic systems.

Organically modified clays and silicaceous materials present drawbacks for thickening organic compositions. Both organically modified clays and fumed silica exist in solid particulate, or powder form, and these materials generally must be added as solids during the grind stage of manufacture of the compositions to be thickened. Dusting problems are associated with the use of such organically—modified clay and especially of, silicaceous products during these manufacturing procedures. The use of these types of additives can also lead to a loss of gloss and aesthetic properties in the final paint or coating. Fumed silica in particular is dusty and difficult to handle because of its low bulk density. Furthermore, these additives cause the systems in which they are incorporated to exhibit extremely rapid recovery following shear, thereby limiting the leveling or smoothness of the applied composition.

Organoclays have sometimes been sold as liquid gels, where the organoclay is dispersed into an organic liquid, in order to avoid the disadvantages of using a solid thickener, but such products have not met wide success.

Some of the problems of use and dispersibility associated with the solid or powder type of thickeners such as organoclays and silica are overcome with the use of polyamide rheological additives. For example, Rheox, Inc. U.S. Pat. No. 4,778,843 describes a solid polyamide rheological additive especially designed for organic solvent-based compositions, which comprises the reaction product of polycarboxylic acid, an active hydrogen compound of a specified carbon chain length and structure, and a monocarboxylic acid capping agent. Recent Rheox U.S. Pat. No. 5,349,011 describes a polyamide-ester rheological additive, especially for organic, solvent-based compositions, which comprises the reaction product of polycarboxylic acid, an active hydrogen composition of a specified structure, an alkoxylated polyol, and a monocarboxylic acid capping agent. Said additive is described as exhibiting excellent efficiency and ease of dispersibility when used in aliphatic solvent-based coating compositions, and as effective when dispersed into a solvent.

Rheox U.S. Pat. No. 5,034,444 describes an anti-sag additive for non-aqueous coating compositions which is the reaction product of an alkoxylated aliphatic nitrogen-containing compound, an aliphatic diamine or mixtures thereof, together with an organic polycarboxylic anhydride or acid, an alkanediol polyepoxide ether or mixtures thereof. The additive is described as providing anti-sag and storage stability properties for high solids organic coating compositions.

Two recent patents issued to Rheox, Inc., on inventions of the inventor of this case, describe liquid pourable rheological additives based on two types of alkoxylated nitrogen-containing chemistry—see U.S. Pat. Nos. 5,536,871 and 5,510,452, the teaching of which are incorporated by reference herein.

U.S. Pat. No. 4,337, 184 describes a rheology modifier useful in water-based and organic solvent-based compositions derived from the reaction of polyalkylene oxide, polyfunctional material which includes polyols, amines, amine alcohols, thiols and polyisocyanates, including diisocyanates and water. The modifiers are characterized by having a branched structure and containing substantially no terminal hydrophobic.

While not a rheological additive, U.S. Pat. No. 4,072,641 describes polyamide resins useful as flexographic ink vehicles which are prepared by reacting polymeric fatty acids, an alkylene diamine, a mono amino alcohol which is neither branched nor ethoxylated, and a chain-stopping agent, which agent includes a particular branched chain monocarboxylic fatty acid. U.S. Pat. No. 5,100,438 describes an ester-amide additive useful for coal-water slurries which is obtained by the reaction of a polycarboxylic acid with a polyether glycol and an aliphatic amine. Salts of these ester-amides are also disclosed. The resulting materials are combined with water, and the water in turn is mixed with the coal in a mixer. The resulting slurries are liquids at ambient temperature.

Rheox U.S. Pat. No. 4,499,233 describes a water-dispersible modified polyurethane polymer as a viscosity increasing composition for aqueous systems. The polymer is discussed as the reaction product of a polyisocyanate, a polyether polyol in a defined molar range, a modifying agent, and a capping agent reactive with the reactive product of the polyisocyanate, the polyether polyol and the modifying agent. Capping agents described include mercaptans, primary and secondary amines and monoisocyanates.

Recent U.S. Pat. No. 5,319,055 shows a thickening agent for thickening solvent-containing compositions described as the reaction product of a polyol containing at least two hydroxyl groups, a polyisocyanate containing at least two isocyanato—groups and an active hydrogen compound having the formula R-X wherein X is selected from the group consisting of primary amino, secondary amino, and hydroxyl, and R represents a group comprising from 1 to 30 carbon atoms. All the active hydrogen compounds shown in the examples are mono-functional except for examples 5 and 15 which have dual functionality. The thickening agents produced are dispersed into solution with toluene prior to being used as thickeners for non-aqueous dispersions.

Levels of polyamide rheological thickening additives varying between 0.1% and about 10%, based on the total weight of the system to be thickened, have been found to be useful. The aforesaid thickeners are in most cases viscosity improvers, and unless mixed with solvents, solid products.

Disadvantages of Current Systems

Commercially available rheological additives for organic systems based on polyamide and similar chemistry have been in the past most often been prepared in solid form, and have been produced and used as thickeners in a dry, solid form. Dispersion is very important to activation of the additive, and viscosity efficiency is a direct function of successful dispersion into the system to be thickened. Problems associated with the use of solid rheological additives, however, include poor dispersibility when added to organic systems. In addition, dust concerns are similar to those encountered with other types of particulate materials, such as fumed silica. When added to organic paints, for example, solid additives by their nature tend to agglomerate and form clumps. Such clumping can be reduced by adding the additive to the system with agitation. Dissolution is often very slow, and often adversely impacts the efficiency of specific manufacturing operations.

Particularly in formulations comprising other chemicals and ingredients of the type found in paint systems, extended agitation and aging periods are required before proper incorporation of solid thickeners is attained. Even when such additives are furnished as diluted solutions, they remain difficult to disperse.

Manufacturers have searched for a more effective way of introducing various thickeners into organic systems. To satisfy this desire, a few commercial polyamide-type thickeners and other rheological additives are today sold for paint and other compositions as liquids. However, these commercial thickening compositions are most often made by dissolving solid rheological additives into an organic liquid medium or solvent. The organic solvent lowers the viscosity of the rheological additive, which itself is non-pourable, to create a liquid mixture in order to provide ease in handling that a liquid brings to a manufacturer. The choice of liquid medium and its amount depends on the desired viscosity of the thickening composition mixture. Typically, the viscosity of the pourable thickening composition mixture ought to be less than about 250–300,000 cP (at 10 RPM with a Brookfield RVT viscometer) so that it will readily pour from the storage container as a liquid, and rapidly incorporate into the system to be thickened at room temperature. The solvent selected for such commercial composition has, up to this time, usually been a volatile organic solvent such as toluene, propanol and butyl CARBITOL®. Ranges of ratios of 20% to 50% rheological additive to 50% to 80% solvent are common for such commercial liquid products.

The use of volatile organic solvents with rheological additives contributes to the overall volatile organic content ("VOC") of the system that will be thickened. Rheological additives are used at relatively low levels in organic and aqueous systems, however they do contribute to the total VOC of the system, because they are typically provided as solutions or dispersions in the aforesaid organic solvent mixtures. This solvent evaporates after products containing such chemicals are applied, and enters the atmosphere during the drying and/or curing of the system. Similar evaporation occurs during the manufacture of inks, sealants, and greases.

The reduction of release of organic vapors in the use of various types of industrial paint applications and in the manufacture of inks, polyesters, and coated articles has become important in combating atmospheric pollution and in improving human health and safety. The United States has imposed increasingly stringent limitations upon the emission of such gases to the atmosphere. These organic vapors have an offensive odor, and cause damage to vegetation, wildlife, and other aspects of the external environment. A recent California statute prohibits the manufacture or sale of any coating which contains more than a defined amount of volatile organic compounds, and other states are following with similar prohibitions. A liquid thickening composition having little or no VOC will contribute little or zero VOC to the system being thickened, while having the pronounced advantage of being pourable.

A pourable thickener, which would be substantially 100% active, containing no or very little solvent, has been perceived heretofore as presenting daunting technical difficulties that led many artisans to conclude that it likely would be impossible to achieve. Rheological additives must provide high levels of viscosity or thickness to systems, which prior to such addition are often less viscous. Some systems, such as grease, must become gel-like as a result of the addition.

Rheological additives must be efficient, even when added at very small relative weight levels, and must therefore have the ability, at such levels, to impart significant increases in viscosity to much larger volumes of organic systems. Rheological additives, in fact, often must impart to systems at very low shear rates a behavior that approaches that of a solid. These requirements led many scientists to conclude that such additives must themselves have very high viscosity levels, and they must be either solid or solid-like. A rheological additive, which could in some circumstances be liquid and pourable, and could at a 100% concentration be less viscous than the system to be thickened (where it would be present at a level of around 3% or less) appeared, and still appears to many scientists, to be a physical impossibility.

Despite the wide variety of rheological additives known in the art, research has been independently and simultaneously conducted toward both active liquid thickeners that are in pourable forms, and which are highly efficient and are readily dispersible in the composition to be thickened; and, in addition, toward non-VOC-containing rheological additives which overcome the deficiencies associated with prior art volatile solvent-mixed thickeners. The present invention satisfies these twin long sought goals.

OBJECT AND SUMMARY OF THE INVENTION

Object of the Invention

It is an object of the present invention to provide a liquid rheological thixotrope which is liquid and easily pourable at room temperature even in the absence of added solvents, for systems including inks, paints, epoxies, polyesters and coatings.

It is a specific object of the present invention to provide a 100% active rheological additive in pourable liquid form which is efficient in thickening and providing rheological properties to organic and solvent compositions.

It is further object of the present invention to provide an improved method of dispersing liquid rheological additives into organic compositions to be thickened.

It is a still further object to provide a thixotrope which will not discolor common coatings systems.

Summary of the Invention

This invention is of a thixotrope, which, when free of diluent, is pourable at ambient temperatures, and which provides effective and efficient thixotropic properties when used at low levels in organic systems, and does not discolor them. Unlike prior additives, this rheological liquid additive is completely rheologically active and efficient, and does not require a diluent to maintain a liquid state. The invention also covers a method of providing improved rheological properties to organic compositions using liquid rheological additives.

The advantages of the present invention over the prior art are quite numerous. These new rheological agents may be solvent-free (zero volatile organic compound ("VOC")), and are easily pourable liquids at ambient temperatures and, therefore, easy to handle. They provide high efficiencies at low shear rates, and provide anti-sag properties to fluid coating films. They are readily dispersible in solvent-based systems, requiring no set minimum or maximum temperature for incorporation. It is believed that the rheological additive of the present invention functions by associative mechanisms by interaction with the pigment and the resins to build structure. The new theological additive does not adversely affect gloss in the coating film.

In one aspect, the present invention provides a rheological additive which comprises the reaction product of: (a) one or more active hydrogen compounds, such as polyols and amino alcohols, wherein the active hydrogen compound contains at least two active hydrogen moieties; (b) one or more compounds containing at least two moieties which are capable of reacting with one of the active hydrogen moieties of (a),and; (c) one or more compounds containing at least three active moieties including at least one moiety capable of reacting with the moiety in excess of (a) and (b) and at least one additional polar moiety. This additive is liquid and pourable at or nearly at 100% active material without the need of a diluent, and provides acceptable rheology and viscosity to a large variety of organic systems at low levels of use.

Further advantages and features of the invention, as well as the scope, nature and utilization of the invention, will become apparent to those of ordinary skill in the art from the description of the preferred embodiment of the invention set forth below:

DESCRIPTION OF THE PREFERRED EMBODIMENTS

The liquid additives of this invention may be made using a variety of materials and by a variety of methods either disclosed hereafter, or which will appear obvious when the disclosure of this patent occurs. Applicants do not intend to limit the materials or methods of manufacture of such additives by the following descriptions.

One aspect of the present invention relates to a liquid rheological additive composition comprising a reaction product obtained from the reaction of:

a) One or more active hydrogen compounds, wherein the active hydrogen compound contains at least two active hydrogen moieties;

b) One or more compounds containing at least two moieties which are capable of reacting with the active hydrogen moieties of (a); and c) One or more compounds containing at least three moieties capable of reaction with a) or b) including at least one moiety capable of reacting with the remaining moiety after reaction of (a) and (b), and at least one additional polar moiety, with the proviso that (c) contain at least three polar moieties, some or all of which may be the result of the reaction to form the additives of this invention.

In the second aspect of this invention the rheological additive composition comprises a reaction product formed from the reaction of:

a) One or more active hydrogen compounds, wherein the active hydrogen compound contains at least two active hydrogen moieties; and b) One or more compounds containing at least two moieties which are capable of reacting with the active hydrogen moieties of (a), wherein compound a) is in stoichiometric excess of compound b);

thereby resulting in a reaction product which retains at least one active hydrogen moiety.

Compounds useful for element a), are selected from polyols, amino alcohols and diamines. Polyols can be selected from any aromatic, aliphatic or cycloaliphatic, straight chain or branched chain, saturated or unsaturated which have at least 2 carbon atoms, and more preferably 2 to 40 carbon atoms. Examples of these are 1,2 ethanediol, 1,2- and 1,3-propanediol, 1,4- and 1,3-butanediol, 1,5-pentanediol, 1,6-hexanediol, 2,5-hexanediol and the like either alone or mixtures thereof. Included in these polyols are dimer diols which are based on dimer acids. Dimer diols are commercially available under the trade name Empol from Henkel Corporation—Emery Group. Illustrative example of a dimer diol is Empol 1075.

Included in polyols useful in this invention are polyether polyols which may be a homopolymer, or a block or random copolymer having the repeating unit:

$$-[OCR_1R_2-CR_3R_4-]- \qquad (I)$$

wherein $R_1$, $R_2$, $R_3$ and $R_4$ of each oxyalkylene unit are independently selected from the group consisting of H, $CH_3$ and $C_2H_5$. The polyether polyols must have a hydroxy functionality at each termini of polyether chain. Exemplary examples of such polyether polyols are polyethylene glycols, polypropylene glycols, poly(ethylene-propylene) glycols and polytetrahydrofurans.

α, ω-Diamino polyethers, such as Jeffamine D-400, represent another important class of active hydrogen compounds useful in the practice of this invention.

Compounds particularly preferred for element a) include alkoxylated aliphatic amine diols and alkoxylated aliphatic amide diols which are liquids at ambient temperatures. These compounds can normally be selected from tertiary amines with one alkyl group and preferably two hydroxyalkyl or polyoxyalkylene groups attached to the nitrogen atom and have a general chemical structure represented by the following formula (II):

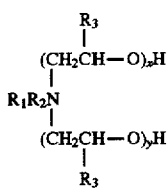

wherein:

R$_1$, which also provides another one of the important functions of the invention, is a pendent straight or branched chain aliphatic alkyl or alkenyl radical having 6 to 40 carbon atoms, preferably 8 to 20 carbon atoms, and most preferably 10 to 18 carbon atoms. Especially preferred is where R$_1$ is a fatty alkyl having 11 to 18 carbon atoms such as coco, stearyl, soya, tallow, hydrogenated tallow, oleyl and mixtures thereof.

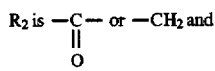

3) R$_3$ is hydrogen or methyl.

The oxyalkylene group which also provides an important function of the invention when using materials of Formula II is represented by

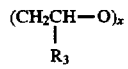

wherein R$_3$ is a hydrogen or methyl group and x is 1 or 2 and is preferably ethoxyl, propoxy or a mixture thereof. At least one of x or y is at least 1 preferably both x and y are at least 1 and the sum of x+y is from 1 to 40, preferably 2 to 30, and most preferably 2 to 20.

Illustrative examples of such alkoxylated aliphatic amine diols useful in this invention, represented by formula (II), are available under the trade name Varonic, from Witco Corporation, and Ethomeen from Akzo Chemie America.

Amino alcohols useful as element (a) of this invention contain one primary or secondary amino group and one hydroxy group. Illustrative examples of useful amino alcohols are monoethanolamine, 2-amino-2-methyl-1-propanol, 3-amino-1-propanol, 2-(2-aminoethoxy)ethanol and mixtures thereof. Higher functionality hydrogen containing compounds with 3 or more active groups may be used as a portion of the total diols; however, their use might be limited in some circumstances since such use might lead to the formation of crosslinked gels which are unsuitable in the environment of the organic formulation in which the invention is to be used.

It is most preferred that compound a) be a compound which is a liquid at ambient temperature in order to maximize the likelihood that a liquid reaction product be obtained although in some cases solids such as 1,6-hexanediol have also proved effective.

Compounds useful for element b) can be any compound containing at least two moieties which are capable of reacting with the active hydrogen moieties of compound a). Preferably, the active functional moiety can be selected from compounds containing carbonyl groups. These compounds are selected from either polycarboxylic acids or polyisocyanates and mixtures thereof with polycarboxylic acids being preferred.

Polycarboxylic acids useful for this invention are to be selected from aromatic, aliphatic or cycloaliphatic straight chain or branched chain, saturated or unsaturated dicarboxylic acids which have at least 2 carbon atoms, and more preferably 3 to 40 carbon atoms. Examples of these are adipic acid, oxalic acid, malonic acid, succinic acid, glutaric acid, pelargonic acid, suberic acid, azelaic acid, undecanedioic acid, 1,11-undecanedicarboxylic acid, dodecanedioic acid, hexadecanedioic acid, docosanedioic acid, maleic acid, fumaric acid and the like with adipic acid being a preferred acid. Likewise, polymeric polyacids, such as polybutadiene dicarboxylic acids, are also useful. The term polycarboxylic acids are also used to include hydroxy substituted dicarboxylic acids and oxadicarboxylic acids. Representative of hydroxy substituted dicarboxylic acids are tartaric acid, citric acid and hydroxyisophthalic acid. Representative of oxadicarboxylic acids are 3,6,9-trioxaundecanedioic acid and polyglycol diacid.

Dicarboxylic acids of oligomers of fatty acids having carbon chain of from 16 to 20 carbon atoms are preferred. Exemplary fatty acids are those derived from soybean oil, tall oil, corn oil, linseed oil, cottonseed oil, castor oil, kapok seed oil, rice bran oil and mixtures thereof. Even further preferred are oligomers of fatty acids which are substantially comprised of dimerized fatty acid, such are often called "dimer acids". These dimerized fatty acids constitute at least 75% by weight of dibasic acid. The oligomerized fatty acid preferably also has a low monomer content such as less than about 8% by weight. The dimerized fatty acids also has a low polybasic acid content such as less than about 20% by weight. These dimer acids are commercially available under the trade name Empol Dimer Acids from Emery Industries, and Pripol Dimer Acids from Unichema, International. Illustrative examples of useful dimer acids are Empol 1004, Empol 1008, Empol 1018, Empol 1016 and the like. Mixtures of polycarboxylic acids can also be employed.

The polyisocyanates which can be employed in this invention contain at least two isocyanate groups per molecule and can be linear or branched aliphatic, aromatic or cycloaliphatic. Such polyisocyanates may also be in the form of a prepolymer having two or more unreacted isocyanate moieties and having an average molecular weight in the range of from about 500 to about 2,000. The polyisocyanate preferably contains two isocyanate moieties per molecule. Higher functionality polyisocyanates may be used as a portion of the total isocyanate requirement. However, the use of higher functionality polyisocyanates is limited by the possibility of the formation of a crosslinked, insoluble gel which is unsuitable for purposes of the present invention.

Exemplary polyisocyanates useful in the preparation of the compositions of the present invention are 1,4-tetramethylene diisocyanate, 1,6-hexamethylene diisocyanate, 2,2,4-trimethyl-1,6-diisocyanatohexane, 1,10-decamethylene diisocyanate, 1,4-cyclohexane diisocyanate, 4,4' methylenebis(isocyanatocyclohexane), 1-isocyanato-3-isocyanatomethyl-3,5,5-trimethylcyclohexane, m- and p-phenylene diisocyanate, 2,6- and 2,4-tolylene diisocyanate, xylene diisocyanate, 4-chloro-1,3phenylene dissocyanate, 4,4'-biphenylene diisocyanate, 4,4'-methylene diphenylisocyanate, 1,5-naphthalene diisocyanate, 1,5-tetrahydronaphthalene diisocyanate, and C$_{36}$dimer acid diisocyanate, based on dimer acids, sold under the trade name "DDI 1410" by Henkel Corporation. Preferred polyisocyanates are 1,6-hexane diisocyanate and C$_{36}$ dimer diisocyanate.

Element c), which is a chain ending unit or agent, or capping agent, is utilized, among other functions, to control the average molecular weight of the polycondensation reaction of elements (a), (b) and (c). Agent (c) should be a substance having two or more moieties capable of reacting with the moiety in excess of (a) and (b) and at least one additional polar moiety. The chain ending unit contains most preferably a branched chain aliphatic, cycloaliphatic or aromatic group, and should be chosen to provide a reaction product which, as an important aspect of the invention, has one or more polar moieties which are capable of interacting with similar moieties on other reaction products, after the reaction is complete, such as by hydrogen bonding or polar-polar interactions.

A. When the reactive moieties of component (a) are in excess, the capping agent should contain at least one moiety capable of reacting with the reactive moieties of component (a).

Also when the ratio of the number of moles of the reactive moieties of compound (a) to the number of moles of the reactive moieties of compound (b) is greater than 1.0, then the capping agent should contain at least one moiety capable of reacting with the reactive moieties of (a).

The amount of the capping agent, employed during the process of this invention should preferably be in an amount sufficient to react with one, or both, or all the reactive moieties of (a) such that the reaction product additives of this invention further contain interactive groups which will influence various functional mechanisms.

B. When the ratio of the number of the reactive moieties of element (a) to the number of moles of the reactive moieties of element (b) is less than 1.0, then the capping agent should contain at least one moiety capable of reacting with the reactive moieties of (b).

When the reactive moiety of component (b) is in excess, the capping agent should contain at least one active hydrogen moiety capable of reacting with the reactive moieties of component (b). Preferably, such capping agent contains an amino moiety. The amine moieties of such preferred capping agents may be primary or secondary.

The amount of the capping agent employed during the process of this invention should be in an amount sufficient to react completely with the reactive moieties of (b) such that the additives of this invention further contain interactive groups which will influence various functional mechanisms.

As stated more generally above, the capping agent contains, in addition to at least one moiety capable of reacting with the reactive moiety or moieties of either component (a) or (b), or a reaction product of a) and b), at least one additional polar moiety which remains capable, after the reaction is complete, of interacting with other moieties via, e.g., hydrogen bonding and/or polar-polar interactions, on other reacted polymers or on other chemical components found in the particular non-aqueous system to be thickened. Examples of such moieties include: hydroxyl, amide, urea and carbamate moieties. Preferred capping agents generally have from 2 to 8 carbon atoms.

For purposes of this invention, the terms "polar moieties", or "interactive moieties" include compounds which contain one or more groupings such as —OH, —CONH$_2$, —CO—NH—, —OCO—NH—, or —CO—NH—CO— which provide (1) electrostatic interactions and/or (2) hydrogen bonding interactions with other like groupings of similar characteristics. As used herein, these groups are believed to involve in various structural attributes which will provide superior thickening efficiencies.

Preferred for element (c) are amino alcohol capping agents containing one primary or secondary amino group which reacts with an excess of the reactive functionality of component (b) and, additionally, contains one or more polar hydroxy group(s), such that the reaction product contains a thermodynamically favored amide or urea moieties. Improved results normally can be obtained if the amino alcohol capping agent is branched. Illustrative examples of useful agents include 2-amino-2-methyl- 1,3-propanediol, 2-amino-2-ethyl- 1,3-propanediol, tris(hydroxymethyl) aminomethane and the like. Non-branched agents such as diethanolamine also are useful. The most preferred capping agents are 2-amino-2-ethyl-1,3-propanediol and tris (hydroxymethyl)aminomethane. It is to be understood that mixtures of chain ending agents of the described type may also be used.

The formula for 2-amino-2-ethyl-1,3-propanediol is as follows:

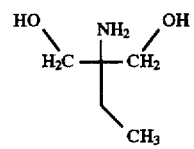

It is to be understood that reactions of the above designated materials which produce a solid reaction product are not included in the object of the invention. Comparative examples showing such solid reaction products are included for completeness in the following examples.

It should be understood that a variety of additional reactions can be used to prepare the polymers of this invention including chain-extending and modifying agents including diamines, most particularly pendant diamines, as long as the final reaction product is a liquid.

It is believed that the compound c), described above, is one of the most important factors in the first aspect of the invention in obtaining the liquid nature of the inventive rheological product.

In the first aspect of the invention, the reaction product is formed from components a), b) and c) as described above wherein the ratio of the sum of the number of reactive moieties in compound a) and in compound c) to the number of reactive moieties in compound b) is generally greater than 1.75. The amount of compound a) found useful may vary from about 10 to 90 parts by weight, amounts of compound b) found useful may vary from about 2 to 97 parts by weight and amounts of compound c) found useful may vary from about 1 to about 40 parts by weight.

In the second aspect of the invention, the inventive rheological compounds are formed from the reaction of a) and b), where b) is selected from a class of b) as defined above. The amount of compound a) may vary from about 15 to 95 parts by weight; amounts of compound b) may vary from about 5 to 85 parts by weight.

The compositions of the present invention are rheological liquids without diluent which effectively impart thixotropic properties to systems in which they are utilized. These properties are equal to previously known solid thixotropes. When used, the additives may contain no solvent, or may optionally contain substantially reduced solvent. The rheological additives of the present invention are a substantial improvement over known additives. In contrast to some particulate-type rheological additives, the rheological additives of the present invention have excellent flow and leveling properties, as well as excellent efficiency and easy dispersing characteristics. Compared to recent solid rheological additives disclosed in the art, the rheological additives of this invention can be incorporated in the system as rheological liquids.

While not bound by any theory, the liquid rheological additives of the present invention are believed to function in part as thickeners by interaction with themselves and with components such as resin and pigment in the system to be thickened. The formation of hydrogen bonding due to the presence of amide and hydroxyl groups in the structure of the additives likely influences the makeup of a random network of high surface area, thereby increasing interaction among the polymers with the resin and the pigment in the composition to be thickened. Such a thickening mechanism may explain why a pourable liquid can at low levels of use provide substantial viscosity to a much larger volume system.

Also the proposed mechanism of associative thickening of systems and solutions is in part through physical interactions between the pendant moieties often associated with compound a) in the thickener molecule. Their associations with one another may create a three dimensional network of thickener molecules that results in a very high viscosity when dispersed into a system. When added to an organic system, the combination of mechanisms in combination with the interactivity of the chain end group allow the thickener to have less association with itself; the thickener molecule then both (i) interacts with and (ii) associates with moieties of the organic composition and with itself, and is thereby believed to thicken in a novel and unusual manner. The rheological additives prior to dispersion is fully liquid of a viscosity that permits pourability.

The liquid rheological additive of the present invention may be used to thicken a variety of organic and solvent-based compositions, and the rheological additive may also be used in solvent-free compositions. Non-aqueous solvents including non-aqueous polymer solutions such as, for example, a solution of an alkyd in mineral spirits, dispersions of polymers in non-aqueous media (called non-aqueous dispersions), and non-aqueous paints, paint strippers, adhesives, inks, sealants, mastics, caulks, pigment dispersions, and pigment printing pastes can be advantageously bodied, viscosified, or thickened, by this invention. The additive is particularly useful, for example, in thickening aliphatic and aromatic solvent-based compositions, and may also be used in polar (ketones, alcohols, esters) based compositions. Illustrative organic compositions include aliphatic alkyd paints such as "trade sales" paints, varnishes, epoxy-based paint, polyesters, modified alkyd based paints and alkyd, polyester and acrylic bake enamels, such as standard quality industrial paints, certain sealants and unsaturated polyester resin formulations. The additives are useful in aromatic high solids bake enamels which include systems based on alkyd/melamine, acrylic/melamine, and polyester/melamine system including appliance enamels, and equipment enamels. Additionally, the additives find use in high solids air-dry enamels based on alkyd and modified alkyd formulations.

In addition to aliphatic and aromatic solvent-based systems, the additives of the present invention may also be used in petroleum-based and vegetable oil-based systems. Representative examples of petroleum solvents include Magiesol 52 sold by Magic Bros., Sunprint HP 750 marketed by Sun Inc., and Exprint 705 sold by Exxon Chemical Company. Illustrative vegetable oils include but are not limited to soybean oil, rapeseed oil, canola oil, palm oil, rice bran oil and the like. The additive of this invention can easily be dispersed into the organic composition to provide improved viscosity characteristics. The additive can be dispersed in the composition at any temperature normally used in their production.

Since the additive is an easily pourable or pumpable rheological liquid, it can be incorporated very easily into a variety of compositions at various stages of their preparation. The compositions of this invention can also be added at any stage of the formulation production. It can be added at the beginning of processing, during processing, or as a post-add ingredient.

The amount of rheological additive used in a specific instance is determined by numerous factors, including the type of the organic solvent-based composition to be thickened, and the level of thickening desired. However, a general range is from about 1.5 to about 30 pounds per hundred gallons of formulation. On a weight basis, the amount of the rheological additive is generally from about 0.1 to about 10% by weight, preferably from about 0.1 to about 8% by weight, more preferably from about 0.1 to about 5% by weight and most preferably from about 0.2% to about 3% by weight of the system to be thickened.

The rheological additive of the present invention may be prepared according to the known polycondensation reaction. The order of the addition of the co-reactants is not generally important, although generally compounds a) and b) should first be reacted to form a prepolymer, prior to addition of compound c), and materials can be added either at ambient temperature or at reaction temperature. For example, the reactants may be charged in increments to a suitable reaction vessel equipped with a mechanical stirrer, a thermometer, a Dean-Stark adapter or other water collector and a nitrogen inlet. The vessel containing the reactants is heated under a blanket of nitrogen. The reaction may be carried out under atmospheric pressure or under vacuum. The reaction temperature to be used in the synthesis depends upon the reactants. Thus, the reaction temperature to be used in the reaction of an active hydrogen compound with a polycarboxylic acid preferably ranges from ambient temperature to 300° C. More preferable, the temperature ranges from ambient to 250° C., and most preferably from 120° C. to 220° C. Water formed during this reaction is removed as condensate as the reaction progresses. After the completion of the reaction, the additive is cooled and discharged. The reaction temperature to be used in the reaction of an active hydrogen compound and an isocyanate preferably ranges from ambient temperature to 150° C. More preferably, the temperature ranges from ambient to 110° C and most preferably from 60° C. to 100° C. After the completion of the reaction, the solvent, if employed, is removed by a rotary evaporator or the solvent was evaporated off at 80° C. in a vacuum oven overnight.

The additives of the present invention may be synthesized with or without a catalyst. The catalyst, if used, may be selected from those which are normally used for condensation reactions. Examples of such catalysts include but not limited to sulfuric acid, p-toluene sulfonic acid, dibutyltin dilaurate, tetra alkyl tin or titanium compounds, metal hydrides and the like. Most preferred catalyst for the reaction of active hydrogen containing compound and dibasic acids is p-toluene sulfonic acid and for the reaction of active hydrogen containing compound and isocyanates is dibutyltin dilaurate and the catalyst should generally be used in an amount of from about 0.001 to 2.5 percent by weight based on the total weight of the reactants.

The additives of the present invention may be manufactured with or without an organic solvent. Since the preferred form of the rheological control agent is a solvent-free pourable liquid, it is preferable to synthesize the product in a solvent free environment. Since the solvent free product is a viscous liquid, it may be appropriate to use a solvent at the let down stage during the synthesis to make the product even more pourable. When a solvent is used during synthesis, the type of solvent is not critical except that it should not be reactive with the components of the thickener of this invention. If it is appropriate to use a solvent during the synthesis, the same solvent used in the coating composition in which the rheological additive could be incorporated may be preferred. Preferred solvents, if used at all, for synthesizing the rheological additives of this invention are ketones such as methyl ethyl ketone, methyl isobutyl ketone, esters such as propylene glycol mono methyl ether acetate, aromatic solvents, such as toluene, xylene, aromatic petroleum distillates and mixtures thereof, aliphatic solvents such as hexane, heptane, cyclohexane and aliphatic petroleum distillates and mixtures thereof. The most preferred solvents are aromatic petroleum distillates such as being sold under the trade name Aromatic 100 by Exxon Chemical Company. A combination of solvents could be employed as long as the solvents are compatible. The solvent should generally be used from 0 to 25 percent by weight of the reaction mixture.

The rheological additives of the present invention can provide important advantages in a variety of organic coating compositions. Since the rheological additives of the present invention are solvent-free (zero VOC) or contain substantially reduced solvent (low VOC) they are thus compatible with all coating, ink, or polyester systems regardless of VOC specification. Since the rheological additives of the present invention are compatible with the systems to be thickened, they are highly dispersible at low activation temperatures in almost all systems. Furthermore, because the rheological additives impart effective rheological properties to compositions, their use enables coating formulations to be prepared which do not unduly sag or flow when applied to vertical surfaces. As added benefits, the rheological additives of the present invention generally do not show any yellowing of the coating composition and above all do not significantly affect the gloss or fineness of grind of the original paint or coating composition.

DESCRIPTION OF TESTS

The present invention is exemplified and compared in the following examples. However, the Examples should not be construed as limiting the invention.

In the following examples, parts are given by weight unless otherwise indicated.

EXAMPLE 1

To a 1 liter 4-necked round bottomed flask equipped with a thermometer, a Dean-Stark adapter, a mechanical stirrer and a nitrogen inlet, 374 parts Empol 1075 and 153.45 parts adipic acid were charged. The mixture is heated to 200° C. with stirring under a blanket of nitrogen. Water starts to come off at 180©C. After an hour at 200° C., aliquots are taken hourly and the acid values are determined. When the acid value is below 83 and constant, 83.41 parts 2-amino-2-ethyl-1,3-propanediol were charged and the reaction continued until the acid and the amine values are below 4. At the end of the reaction, the product was cooled and discharged. The product was cooled to ambient temperatures and was a liquid.

Infrared analysis of the product indicated the presence of ester band at 1738 cm$^{-1}$ and amide band at 1667 cm$^{-1}$. Molecular weight analysis with GPC methods against a polyethylene glycol standard indicated a weight average molecular weight of 3620 and a number average molecular weight of 1870.

EXAMPLES 2-12

The general procedure outlined in Example 1 was used, except that the reactants were replaced as indicated in Table 1. All examples were pourable liquids at ambient temperature.

TABLE 1

| Example | Reagents | Parts by wt | Acid Value* | Amine Value* |
|---|---|---|---|---|
| 2 | 1,6-Hexanediol | 35.45 | | |
|  | Adipic Acid | 65.76 | | |
|  | 2-Amino-2-ethyl-1,3-propanediol | 3.75 | 3 | 4 |
| 3 | Polypropylene glycol (mol. wt. 425) | 63.75 | | |
|  | Adipic Acid | 32.88 | | |
|  | 2-Amino-2-ethyl-1,3-propanediol | 17.87 | 3 | 2 |
| 4 | Polypropylene glycol (mol. wt. 725) | 72.50 | | |
|  | Adipic Acid | 21.92 | | |
|  | 2-Amino-2-ethyl-1,3-propanediol | 11.92 | 4 | 1 |
| 5 | Polypropylene glycol (mol. wt. 1000) | 80.00 | | |
|  | Adipic Acid | 17.54 | | |
|  | 2-Amino-2-ethyl-1,3-propanediol | 9.53 | 4 | 2 |
| 6 | Polypropylene glycol (mol. wt. 2000) | 100.0 | | |
|  | Adipic Acid | 10.96 | | |
|  | 2-Amino-2-ethyl-1,3-propanediol | 5.96 | 5 | 4 |
| 7 | Polypropylene glycol (mol. wt. 3000) | 120.0 | | |
|  | Adipic Acid | 8.77 | | |
|  | 2-Amino-2-ethyl-1,3-propanediol | 4.77 | 7 | 1 |
| 8 | Polyethylene glycol (mol. wt. 600) | 72.00 | | |
|  | Adipic Acid | 26.31 | | |
|  | 2-Amino-2-ethyl-1,3-propanediol | 14.30 | 2 | 2 |
| 9 | Jeffamine D-400 | 82.05 | | |
|  | Adipic Acid | 43.84 | | |
|  | 2-Amino-2-ethyl-1,3-propanediol | 23.83 | 1 | 5 |
| 10 | Jeffamine D-2000 | 100.0 | | |
|  | Adipic Acid | 10.96 | | |
|  | 2-Amino-2-ethyl-1,3-propanediol | 5.96 | 5 | 3 |
| 11 | Poly THF mol. wt. 650 | 76.08 | | |
|  | Adipic Acid | 26.31 | | |
|  | 2-Amino-2-ethyl-1,3-propanediol | 14.30 | 5 | 5 |
| 12 | Poly THF (mol. wt. 1000) | 99.90 | | |
|  | Adipic Acid | 21.92 | | |
|  | 2-Amino-2-ethyl-1,3-propanediol | 11.92 | 5 | 1 |

*The acid and the amine values indicated are for the final product.

Comparative Example A

As a comparative example, a 250 ml 4-necked round bottomed flask equipped with a thermometer, a Dean-Stark adaptor, a mechanical stirrer and a nitrogen inlet, 87.0 parts polyethylene glycol mol.wt. 1450 and 13.15 parts adipic acid were charged. The mixture is heated to 200° C. with stirring under a blanket of nitrogen. Water starts to come off at 180° C. After an hour at 200° C., an aliquot is taken hourly and the acid value is determined. When the acid value is below 55 and constant, 7.15 parts 2-amino-2-ethyl-1,3-propanediol were charged and the reaction continued until the acid and the amine values are below 5. At the end of the reaction, the product is cooled to 120° C. and discharged. The product was cooled to ambient temperature and was a solid.

Comparative Examples B and C

Further comparative examples were produced. The general procedure outlined in Comparative Example A is used except that the reactants were replaced as indicated in Table 2. Both products were solids.

TABLE 2

| Example | Reagents | Parts by wt | Acid Value* | Amine Value* |
|---|---|---|---|---|
| Comparative Example B | Polyethylene glycol (mol. wt. 3350) | 100.50 | | |
| | Adipic Acid | 6.58 | | |
| | 2-Amino-2-ethyl-1,3-propanediol | 3.58 | 9 | 4 |
| Comparative Example C | Poly THF (mol. wt. 2000) | 100.00 | | |
| | Adipic Acid | 10.96 | | |
| | 2-Amino-2-ethyl-1,3-propanediol | 5.96 | 5 | 3 |

*The acid and the amine values indicated are for the final product.

EXAMPLE 13–24

The general procedure outlined in Example 1 is used, except that the reactants were replaced as indicated in Table 3. All examples were pourable liquids at ambient temperature.

TABLE 3

| Example | Reagents | Parts by wt | Acid Value* | Amine Value* |
|---|---|---|---|---|
| 13 | Empol 1075 | 64.44 | | |
| | Empol 1004 | 102.06 | | |
| | 2-Amino-2-ethyl-1,3-propanediol | 14.30 | 4 | 1 |
| 14 | 1,6-Hexanediol | 11.82 | | |
| | Empol 1004 | 85.05 | | |
| | 2-Amino-2-ethyl-1,3-propanediol | 11.92 | 1 | 1 |
| 15 | Polypropylene glycol (mol. wt. 425) | 42.50 | | |
| | Empol 1004 | 85.05 | | |
| | 2-Amino-2-ethyl-1,3-propanediol | 11.92 | 4 | 5 |
| 16 | Polypropylene glycol (mol. wt. 725) | 43.50 | | |
| | Empol 1004 | 51.03 | | |
| | 2-Amino-2-ethyl-1,3-propanediol | 7.15 | 2 | 2 |
| 17 | Polypropylene glycol (mol. wt. 1000) | 60.00 | | |
| | Empol 1004 | 51.03 | | |
| | 2-Amino-2-ethyl-1,3-propanediol | 7.15 | 5 | 2 |
| 18 | Polypropylene glycol (mol. wt. 2000) | 80.00 | | |
| | Empol 1004 | 34.02 | | |
| | 2-Amino-2-ethyl-1,3-propanediol | 4.77 | 5 | 2 |
| 19 | Polypropylene glycol (mol. wt. 3000) | 90.00 | | |
| | Empol 1004 | 25.52 | | |
| | 2-Amino-2-ethyl-1,3-propanediol | 3.57 | 7 | 1 |
| 20 | Polyethylene glycol (mol. wt. 600) | 48.00 | | |
| | Empol 1004 | 68.04 | | |
| | 2-Amino-2-ethyl-1,3-propanediol | 9.53 | 4 | 3 |
| 21 | Jeffamine D-400 | 32.82 | | |
| | Empol 1004 | 68.04 | | |
| | 2-Amino-2-ethyl-1,3-propanediol | 9.53 | 3 | 4 |
| 22 | Jeffamine D-2000 | 80.00 | | |
| | Empol 1004 | 34.02 | | |
| | 2-Amino-2-ethyl-1,3-propanediol | 4.77 | 6 | 2 |
| 23 | Poly THF (mol. wt. 650) | 50.72 | | |
| | Empol 1004 | 68.04 | | |
| | 2-Amino-2-ethyl-1,3-propanediol | 9.53 | 4 | 4 |
| 24 | Poly THF (mol. wt. 1000) | 59.94 | | |
| | Empol 1004 | 51.03 | | |
| | 2-Amino-2-ethyl-1,3-propanediol | 7.15 | 4 | 3 |

*The acid and the amine values indicated are for the final product.

Comparative Example D

As a comparative example, a 250 ml 4-necked round bottomed flask equipped with a thermometer, a Dean-Stark adaptor, a mechanical stirrer and a nitrogen inlet, 72.5 parts polyethylene glycol mol.wt. 1450 and 42.53 parts Empol 1004 were charged. The mixture is heated to 200° C. with stirring under a blanket of nitrogen. Water starts to come off at 180° C. After an hour at 200° C., an aliquot is taken hourly and the acid value is determined. When the acid value is below 55 and constant, 5.96 parts 2-amino-2-ethyl-1,3-propanediol were charged and the reaction continued until the acid and the amine values are below 5. At the end of the reaction, the product is cooled to 120° C. and discharged. The product was cooled to ambient temperature and was a solid.

Comparative Examples E and F

Further comparative examples were produced. The general procedure outlined in Comparative Example D is used except that the reactants were replaced as indicated in Table 4. Both products were solids.

TABLE 4

| Example | Reagents | Parts by wt | Acid Value* | Amine Value* |
|---|---|---|---|---|
| Comparative Example E | Polyethylene glycol (mol. wt. 3350) | 100.50 | | |
| | Empol 1004 | 25.52 | | |
| | 2-Amino-2-ethyl-1,3-propanediol | 3.57 | 4 | 5 |
| Comparative Example F | Poly THF mol. wt. 2000 | 80.56 | | |
| | Empol 1004 | 34.02 | | |
| | 2-Amino-2-ethyl-1,3-propanediol | 4.77 | 4 | 2 |

*The acid and the amine values indicated are for the final product.

EXAMPLE 25

A 250 mL three-necked round bottom flask equipped with a mechanical stirrer, a thermometer, a water-cooled condenser, and a nitrogen gas inlet is charged with 42.74 parts Empol 1075 and 100 mL toluene. The reaction mixture was stirred under a nitrogen blanket. Empol 1075 in toluene was then heated to 110° C. to azeotropically distill any water which was present in the solution. The solution was cooled to 70° C. and 20.18 parts 1,6-hexamethylene diisocyanate and 0.001 part dibutyl tin dilaurate were charged to the reaction vessel. The reaction mixture is maintained at 70° C. for two hours. After two hours, 9.53 parts 2-amino-2-ethyl-1,3-propanediol was charged and the reaction was continued at 70° C. for another two hours. The product was cooled to 50° C. and the solvent was evaporated off at 80° C. in a vacuum oven overnight. The product was a very viscous gel.

EXAMPLE 26–28

The general procedure outlined in Example 25 is used, except that the reactants were replaced as indicated in Table 5. All examples are very viscous gels at ambient temperatures.

TABLE 5

| Example | Reagents | Parts by wt |
|---|---|---|
| 26 | Poly THF mol. wt. 650 | 44.38 |
|  | 1,6-hexamethylene diisocyanate | 17.66 |
|  | 2-Amino-2-ethyl-1,3-propanedio | 8.34 |
| 27 | Poly THF mol. wt. 1000 | 49.95 |
|  | 1,6-hexamethylene diisocyanate | 12.62 |
|  | 2-Amino-2-ethyl-1,3-propanediol | 5.96 |
| 28 | Poly THF mol. wt. 2000 | 60.42 |
|  | 1,6-hexamethylene diisocyanate | 7.57 |
|  | 2-Amino-2-ethyl-1,3-propanediol | 3.57 |

EXAMPLE 29–34

The general procedure outlined in Example 25 is used, except that the reactants were replaced as indicated in Table 6. All examples were viscous pourable liquids at ambient temperatures.

TABLE 6

| Example | Reagents | Parts by wt |
|---|---|---|
| 29 | Polypropylene glycol (mol. wt. 425) | 42.50 |
|  | 1,6-hexamethylene diisocyanate | 25.23 |
|  | 2-Amino-2-ethyl-1,3-propanediol | 11.92 |
| 30 | Polypropylene glycol (mol. wt. 725) | 43.50 |
|  | 1,6-hexamethylene diisocyanate | 15.14 |
|  | 2-Amino-2-ethyl-1,3-propanediol | 7.15 |
| 31 | Polypropylene glycol (mol. wt. 1000) | 50.00 |
|  | 1,6-hexamethylene diisocyanate | 12.62 |
|  | 2-Amino-2-ethyl-1,3-propanediol | 5.96 |
| 32 | Polypropylene glycol (mol. wt. 2000) | 60.00 |
|  | 1,6-hexamethylene diisocyanate | 7.57 |
|  | 2-Amino-2-ethyl-1,3-propanediol | 3.57 |
| 33 | Polypropylene glycol (mol. wt. 3000) | 60.00 |
|  | 1,6-hexamethylene diisocyanate | 5.05 |
|  | 2-Amino-2-ethyl-1,3-propanediol | 2.38 |
| 34 | Polyethylene glycol (mol. wt. 600) | 48.00 |
|  | 1,6-hexamethylene diisocyanate | 20.18 |
|  | 2-Amino-2-ethyl-1,3-propanediol | 9.53 |

Comparative Examples H and I

As comparative examples, the general procedure outlined in Example 25 is used except that the reactants were replaced as indicated in Table 7. Both products were solids at ambient temperature.

TABLE 7

| Example | Reagents | Parts by wt |
|---|---|---|
| Comparative Example H | Polyethylene glycol (mol. wt. 1450) | 58.00 |
|  | 1,6-hexamethylene diisocyanate | 10.09 |
|  | 2-Amino-2-ethyl-1,3-propanediol | 4.77 |
| Comparative Example I | Polyethylene glycol (mol. wt. 3350) | 67.00 |
|  | 1,6-hexamethylene diisocyanate | 5.05 |
|  | 2-Amino-2-ethyl-1,3-propanediol | 2.38 |

Comparative Example J

As a comparative example, a 250 mL three-necked round bottom flask equipped with a mechanical stirrer, a thermometer, a water-cooled condenser, and a nitrogen gas inlet is charged with 41.03 parts Jeffamine D-400 and 110mL toluene. The reaction mixture was stirred under a nitrogen blanket. 25.23 Parts 1,6-hexamethylene diisocyanate were added slowly to the reaction vessel. As the addition proceeds the temperature of the reaction mixture slowly increased and reached 57° C. The reaction mixture is maintained at 70° C for one hour. After an hour at 70° C, the reaction mixture was cooled down to 57° C. and then 11.92 parts 2-amino-2-ethyl-1,3-propanediol was slowly charged when the reaction temperature increased to 73° C. and the mixture thickened. The reaction was continued at 70° C. for another two hours. The product was cooled to 50° C. and the solvent was evaporated off at 80° C. in a vacuum oven overnight. The product was a solid at ambient temperature.

Comparative Example K

A further comparative example was produced. The general procedure outlined in Comparative Example J is used except that the reactants were replaced as indicated in Table 8. The product was a solid at ambient temperature.

TABLE 8

| Example | Reagents | Parts by wt |
|---|---|---|
| Comparative Example K | Jeffamine D-2000 | 60.00 |
|  | 1,6-hexamethylene diisocyanate | 7.57 |
|  | 2-Amino-2-ethyl-1,3-propanediol | 3.57 |

EXAMPLE 35–46

The general procedure outlined in Example 25 is used, except that the reactants were replaced as indicated in Table 9.

TABLE 9

| Example | Reagents | Parts by wt |
|---|---|---|
| 35 | Empol 1075 | 21.37 |
|  | DDI 1410 | 36.00 |
|  | 2-Amino-2-ethyl-1,3-propanediol | 4.76 |
| 36 | Polypropylene glycol (mol. wt. 425) | 21.25 |
|  | DDI 1410 | 45.00 |
|  | 2-Amino-2-ethyl-1,3-propanediol | 5.96 |
| 37 | Polypropylene glycol (mol. wt. 725) | 29.00 |
|  | DDI 1410 | 36.00 |
|  | 2-Amino-2-ethyl-1,3-propanediol | 4.77 |
| 38 | Polypropylene glycol (mol. wt. 1000) | 30.00 |
|  | DDI 1410 | 27.00 |
|  | 2-Amino-2-ethyl-1,3-propanediol | 3.57 |
| 39 | Polypropylene glycol (mol. wt. 2000) | 40.00 |
|  | DDI 1410 | 18.00 |
|  | 2-Amino-2-ethyl-1,3-propanediol | 2.38 |
| 40 | Polypropylene glycol (mol. wt. 3000) | 45.00 |
|  | DDI 1410 | 13.50 |
|  | 2-Amino-2-ethyl-1,3-propanediol | 1.79 |
| 41 | Polyethylene glycol (mol. wt. 600) | 24.00 |
|  | DDI 1410 | 36.00 |
|  | 2-Amino-2-ethyl-1,3-propanediol | 4.77 |
| 42 | Jeffamine D-400 | 24.62 |
|  | DDI 1410 | 54.00 |
|  | 2-Amino-2-ethyl-1,3-propanediol | 7.15 |
| 43 | Jeffamine D-2000 | 40.00 |
|  | DDI 1410 | 18.00 |
|  | 2-Amino-2-ethyl-1,3-propanediol | 2.38 |
| 44 | Poly THF mol. wt. 650 | 31.70 |
|  | DDI 1410 | 45.00 |
|  | 2-Amino-2-ethyl-1,3-propanediol | 5.96 |

TABLE 9-continued

| Example | Reagents | Parts by wt |
|---|---|---|
| 45 | Poly THF mol. wt. 1000 | 39.96 |
|  | DDI 1410 | 36.00 |
|  | 2-Amino-2-ethyl-1,3-propanediol | 4.77 |
| 46 | Poly THF mol. wt. 2000 | 40.28 |
|  | DDI 1410 | 18.00 |
|  | 2-Amino-2-ethyl-1,3-propanediol | 2.38 |

The following examples demonstrate the second aspect of the invention

EXAMPLE 47

A 250 mL three-necked round bottom flask equipped with a mechanical stirrer, a thermometer, a water-cooled condenser, and a nitrogen gas inlet is charged with 37.98 parts Ethomeen C-15 and 140 mL methylisobutyl ketone. The reaction mixture was stirred under a nitrogen blanket. Ethomeen C-15 in methylisobutyl ketone was then heated to 120° C. to azeotropically distill any water which was present in the solution. The solution was cooled to 60° C. and 36.00 parts DDI 1410 and 0.001 part dibutyl tin dilaurate were charged to the reaction vessel. The reaction mixture is maintained at 90° C. for two to three hours. The product was cooled to 50° C. and the solvent was evaporated off at 80° C. in a vacuum oven overnight. The product was a liquid.

The general procedure outlined in Example 47 was used, except that the reactants were replaced as indicated in Table 10. All examples were viscous pourable liquids at ambient temperatures.

TABLE 10

| Example | Reagents | Parts by wt |
|---|---|---|
| 48 | Ethomeen C-15 | 67.52 |
|  | 1,6-Hexamethylene diisocyanate | 20.18 |
| 49 | Ethomeen C-15 | 42.20 |
|  | DDI 1410 | 45.00 |
| 50 | Ethomeen C-15 | 63.30 |
|  | 1,6-Hexamethylene diisocyanate | 20.18 |
| 51 | Ethomeen C-15 | 67.52 |
|  | 1,6-Hexamethylene diisocyanate | 21.03 |
| 52 | Ethomeen C-15 | 67.52 |
|  | 1,6-Hexamethylene diisocyanate | 19.51 |
|  | DDI 1410 | 2.40 |
| 53 | Ethomeen C-15 | 63.30 |
|  | Isophorone diisocyanate | 22.23 |
| 54 | Ethomeen C-15 | 50.64 |
|  | Isophorone diisocyanate | 22.32 |
| 55 | Ethomeen C-15 | 67.52 |
|  | 1,6-Hexamethylene diisocyanate | 18.84 |
|  | DDI 1410 | 4.80 |

EXAMPLE 56

A 250 mL three-necked round bottom flask equipped with a mechanical stirrer, a thermometer, a water-cooled condenser, and a nitrogen gas inlet is charged with 67.52 parts Ethomeen C-15 and 140 mL methylethyl ketone. The reaction mixture was stirred under a nitrogen blanket. Ethomeen C-15 in methylethyl ketone was then heated to 85° C. to azeotropically distill any water which was present in the solution. The solution was cooled to 50° C. and 19.51 parts, 1,6-hexamethylene diisocyanate and 2.4 parts DDI 1410 and 0.001 part dibutyl tin dilaurate were charged to the reaction vessel. The reaction mixture is maintained at 75° C. for three to four hours. The product was cooled to 50° C. and the solvent was evaporated off at 70° C. in a vacuum oven overnight. The product was a liquid.

EXAMPLE 57

A 250 mL three-necked round bottom flask equipped with a mechanical stirrer, a thermometer, a water-cooled condenser, and a nitrogen gas inlet is charged with 62.67 parts Ethomeen C-15 and 140 mL methylethyl ketone. The reaction mixture was stirred under a nitrogen blanket. Ethomeen C-15 in methylethyl ketone was then heated to 86° C. to azeotropically distill any water which was present in the solution. The solution was cooled to 50° C. and 0.25 parts isophorone diamine was charged. Then 20.18 parts, 1,6-hexamethylene diisocyanate and 0.001 part dibutyl tin dilaurate were charged to the reaction vessel. The reaction mixture is maintained at 75° C. for three to four hours. The product was cooled to 50° C. and the solvent was evaporated off at 70° C. in a vacuum oven overnight. The product was a liquid.

The general procedure outlined in Example 57 was used, except that the reactants were replaced as indicated in Table 11. All examples were viscous liquids at ambient temperatures.

TABLE 11

| Example | Reagents | Parts by wt |
|---|---|---|
| 58 | Ethomeen C-15 | 61.40 |
|  | Isophorone diamine | 0.70 |
|  | 1,6-hexamethylene diisocyanate | 20.18 |

Comparative Examples L,M and N

As comparative examples, the general procedure outlined in Example 35 is used except that the reactants were replaced as indicated in Table 12. All reaction products were solids at ambient temperatures.

TABLE 12

| Example | Reagents | Parts by wt |
|---|---|---|
| Comparative Example L | 1,6-Hexanediol | 5.91 |
|  | DDI 1410 | 45.00 |
|  | 2-Amino-2-ethyl-1,3-propanediol | 5.96 |
| Comparative Example M | Polyethylene glycol (mol. wt. 1450) | 43.50 |
|  | DDI 1410 | 27.00 |
|  | 2-Amino-2-ethyl-1,3-propanediol | 3.57 |
| Comparative Example N | Polyethylene glycol (mol. wt. 3350) | 67.00 |
|  | DDI 1410 | 18.00 |
|  | 2-Amino-2-ethyl-1,3-propanediol | 2.38 |

EVALUATION OF RHEOLOGICAL ADDITIVES

All the materials prepared according to Examples 1–58 were incorporated by dispersing into a low VOC epoxy-polyamide two component system at a loading of 5 pounds per hundred gallons (pphg) and a number of tests were conducted to demonstrate the effectiveness of the respective rheological additive.

The preparation and components of a high solids polyester-melamine bake enamel paint is described in Formulation A. The ingredients were mixed using a Dispermat model CV, high speed dissolver fitted with a heavy duty 50 mm diameter impeller.

After the paints were made, they were allowed to equilibrate at room temperature overnight, and the paint properties were measured as described below:

(1) Fineness of grind (indicative of dispersibility) was measured in Hegman units using a wide path Hegman gauge in accordance with ASTM D 1210-79.

(2) Brookfield viscosities at 10 and 100 RPM were measured with a Brookfield Model RVT viscometer in accordance with ASTM D2196-81. From viscosity data, a Thixotropic Index (TI) was calculated as follows:

Thixotropic Index (TI)=10 RPM Viscosity÷100 RPM Viscosity (3) Sag resistance was measured in mils using a Leneta Sag multi notch applicator at room temperature in accordance with ASTM D4400-84.

(4) In some instances Stormer viscosities were measured in Krebs Units (KU) with a Thomas Stormer Instrument, Model #09730-G15, in accordance with ASTM D562-81.

(5) Gloss measurements were measured at 60° and/or 20° in accordance with ASTM

D523-80. Drawdowns were prepared of paints according to Formulation A, and the 60° and/or 20° gloss determined after curing the film for 24 hours at room temperature.

(6) Color values were measured on a Hunterlab Model D25-9 colorimeter in accordance
with ASTM E-308.

Additionally, samples of rheological additives of the present invention were evaluated for Brookfield and Stormer viscosities, sag and gloss using the procedure discussed previously in a low VOC epoxy-polyamide two component paint system at a loading of 5 pphg. The preparation and components of the low VOC epoxy-polyamide two component paint system are described in Formulation D, below.

The results of the tests are set forth in Table 16 and Table 17.

Comparative Example 1

A high solids polyester bake enamel paint was prepared according to the procedure described in Formulation A without the addition of a rheological additive. The paint properties were evaluated and are set forth in Table 13.

FORMULATION A
HIGH SOLIDS POLYESTER-MELAMINE BAKE ENAMEL PAINT

| Material | Generic Name | Manufacturer | Parts By Weight |
|---|---|---|---|
| Cargil 154-1297 | Oil free polyester resin Rheological Additive | CARGILL INC. | 526.6 7.4 |
| TITANOX 2101 | Titanium Dioxide | KRONOS, INC | 41.7 |
| Grind at 5,000 RPM for 15 minutes while maintaining the temperature at 125° F. | | | |
| Let down | | | |
| Melamine 23-2347 | Melamine resin | CARGILL INC. | 215.1 |
| Nacure 2501 | p-Toluene sulfonic acid solution | KING INDUSTRIES | 14.8 |

Mix 5 minutes at slow speed (2000 RPM).

Additionally, samples of rheological additives of the present invention were evaluated for Brookfield and Stormer viscosities, sag and gloss using the procedure discussed previously in an epoxy topcoat paint system at a loading of 5 pphg. The preparation and components of the topcoat paint are described in Formulation B.

Rheological additives prepared in accordance with Example 1 set forth above were incorporated into the epoxy topcoat bake enamel paint and the results are described in Table 14.

Comparative Example 2

An epoxy topcoat bake enamel paint was prepared according to the procedures described in Formulation B without the addition of a theological additive. The paint properties were evaluated and are set forth in Table 14.

FORMULATION B
EPOXY TOPCOAT BAKE ENAMEL PAINT

| Material | Generic Name | Manufacturer | Parts by Wt |
|---|---|---|---|
| COMPONENT A | | | |
| Epon 1001 X75 | Epoxy resin | SHELL CHEMICAL CO. | 331.5 |
| PM Acetate | Solvent | ASHLAND CHEMICAL CO. | 86.0 |
| Beetle 216-8 | Urea formaldehyde resin | AMERICAN CYANAMID | 15.2 |
| Nuosperse 700 | Phosphate ester surfactant | HÜLS AMERICA, INC. | 7.6 |
| KRONOS 2101 | Titanium Dioxide Rheological Additive | KRONOS, INC | 316.6 10.0 |
| Grind, high speed disperser for 15 minutes @5000 RPM, then add | | | |
| PM Acetate | Solvent | ASHLAND CHEMICAL CO. | 152.1 |
| COMPONENT B | | | |
| Epon Curing Agent C-111 | Polyamine Adduct | SHELL CHEMICAL CO. | 132.2 |
| PM Acetate | Solvent | ASHLAND CHEMICAL CO. | 35.5 |

Mix 5.4 parts of Component A and 1 part of Component B

TABLE 13

| | Results in High Solids Polyester Bake Enamel Paint Loading: 5 pphg | | | | | |
|---|---|---|---|---|---|---|
| Example | Hegman Grind | Brookfield Viscosity, cP 10 RPM/100 RPM | TI | Leneta Sag(mil) | Stormer (KU) | Gloss 20°/60° |
| 1 | 5 A | 4,600/2,560 | 1.80 | 8 | 111 | 95/103 |
| COMPARATIVE EXAMPLE 1 | 7 A | 1,820/1,834 | 0.99 | <3 | 106 | 89/98 |

TABLE 14

Results in an Epoxy Topcoat paint System
Reacted Paint
Loading: 5 pphg

| Example | Hegman Grind | Brookfield Viscosity, cP 10 RPM/100 RPM | TI | Leneta Sag(mil) | Stormer (KU) | Gloss 20°/60° |
|---|---|---|---|---|---|---|
| 1 | 6 B | 1,000/400 | 2.50 | 6 | 66 | 54/79 |
| COMPARATIVE EXAMPLE 2 | 6 A | 1,000/384 | 2.60 | 3 | 65 | 62/81 |

Samples of rheological additives prepared in accordance with Examples set forth above were incorporated in an epoxy trowling compound, the preparation and components of which are described in Formulation C.

Comparative Example 3

An epoxy trowling compound was prepared according to the procedures described in Formulation C without the addition of a rheological additive. The paint properties were evaluated and are set forth in Table 15.

FORMULATION C
EPOXY TROWLING COMPOUND

| Material | Generic Name | Manufacturer | Parts By wt |
|---|---|---|---|
| PART A | | | |
| Dow D.E.R. 325 | Epoxy Resin | DOW CHEMICAL CO. | 245.0 |
|  | Rheological Additive |  | 5.0 |
| Mix at 3,000 RPM for 5 minutes and then add | | | |
| KRONOX 2160 | Titanium Dioxide | KRONOS, INC. | 50.0 |
| Micromite | Calcium Carbonite | ECC AMERICA, INC. | 200.0 |
| Grind, high speed disperser for 15 minutes at 5000 RPM, while maintaining the temperature at 135° F. | | | |
| PART B | | | |
| P.E.H. 24 | Triethylene tetramine (TETA) | DOW CHEMICAL CO. | 20.5 |

Mix 100 parts of PART A and 7 parts of PART B and shake for 5 minutes in a Red Devil Agitator.

TABLE 15

RESULTS OF COLOR EVALUATION IN AN EPOXY TROWEL COMPOUND

| Example | L* | a* | b* |
|---|---|---|---|
| 1 | 95.14 | −0.29 | 1.17 |
| COMPARATIVE EXAMPLE 3 | 95.08 | −0.27 | 1.10 |

L*measures lightness and varies from 100 for perfect white to zero for black.
a*measures redness when plus, and greenness when minus.
b*measures yellowness when plus and blueness when minus.

COMPARATIVE EXAMPLE 4

A low VOC epoxy-polyamide two component paint was prepared according to the procedures described in Formulation D without the addition of a rheological additive. The paint properties were evaluated and are set forth in Table 16.

FORMULATION D
0.6 (lbs/gal) VOC EPOXY-POLYAMIDE TWO COMPONENT COATING

| Material | Generic Name | Manufacturer | Parts By wt |
|---|---|---|---|
| PART A | | | |
| Epon 828 | Epoxy resin | SHELL CHEMICAL CO. | 343.8 |
| Silicon Resin | Silicon resin SR 882 solution | G.E. SILICONE | 7.0 |
| Nuosperse 700 | Phosphate ester surfactant | HÜLS AMERICA, INC. | 1.0 |
|  | Rheological Additive |  | 14.3 |
| Mix for 5 minutes at 3000 RPM, then add | | | |
| TITANOX 2101 | Titanium Dioxide | KRONOS, INC. | 380.0 |
| Xylene | Solvent | ASHLAND CHEMICAL CO. | 26.0 |
| Disperse at 5,000 RPM for 15 minutes at 130° F, reduce speed to 1,500 RPM and add | | | |
| Epon 828 | Epoxy resin | SHELL CHEMICAL CO. | 115.2 |
| Mix at 1,500 RPM for 3 minutes and cool. | | | |
| PART B | | | |
| Ancamide 506 | Amido Amine | PACIFIC ANCHOR CHEMICAL | 129.0 |
| Ancamide 1693 | Cycloaliphatic Amine | PACIFIC ANCHOR CHEMICAL | 129.0 |
| Toluene | Solvent | ASHLAND CHEMICAL CO. | 32.0 |

Shake 10 minutes in a Red Devil Agitator.
Mix 226 parts of Part A and 74 parts of Part B and shake for 3 minutes on a Red Devil Agitator.

TABLE 16

Results in a 0.6 (lbs/gal) VOC Epoxy-Polyamide two component system
Loading: 5 pphg

| | BASE PAINT | | | | CURED PAINT | | | | |
|---|---|---|---|---|---|---|---|---|---|
| Example | Brookfield Viscosity, cP 10 RPM/100 RPM | TI | Leneta Sag (mil) | Hegman Grind | Brookfield Viscosity, cP 10/100 RPM | TI | Stormer [KU] | Leneta Sag (mil) | Gloss 20°/60° |
| 1 | 20,000/9,400 | 2.12 | 4 | 5A | 1,450/1,180 | 1.23 | 97 | 5 | 96/99 |
| 2 | 16,000/8,600 | 1.86 | 8 | 6B | 1,400/1,240 | 1.13 | 97 | 3 | 97/99 |
| 3 | 8,000/5,200 | 1.54 | 4 | 7A | 1,200/1,140 | 1.05 | 97 | <3 | 98/100 |
| 4 | 12,000/5,600 | 2.14 | <3 | 7A | 1,600/1,446 | 1.11 | 97 | <3 | 98/100 |
| 5 | 20,000/8,200 | 2.44 | 6 | 7A | 1,200/1,100 | 1.09 | 99 | 3 | 101/101 |
| 6 | 22,400/8,800 | 2.55 | 18 | 7A | 1,400/1,260 | 1.11 | 101 | 3 | 100/101 |
| 7 | 28,000/10,200 | 2.75 | 25 | 7A | 1,200/1,100 | 1.09 | 99 | <3 | 99/100 |
| 8 | 17,600/8,600 | 2.05 | 12 | 7A | 1,220/1,145 | 1.07 | 98 | <3 | 98/100 |
| 9 | 22,000/10,000 | 2.2 | 24 | 6B | 1,450/1,260 | 1.15 | 99 | <3 | 98/99 |
| 10 | 42,000/12,800 | 3.28 | 40 | 7A | 1,300/1,210 | 1.07 | 98 | <3 | 99/101 |
| 11 | 8,000/5,000 | 1.6 | 4 | 7A | 1,200/1,160 | 1.03 | 101 | <3 | 99/100 |
| 12 | 10,000/5,800 | 1.72 | <3 | 7A | 1,000/1,080 | 0.93 | 96 | <3 | 100/101 |
| COMPARATIVE EXAMPLE A | Not tested - solid | | | | | | | | |
| COMPARATIVE EXAMPLE B | 8,000/5,800 | 1.38 | 4 | 7A | 1,000/1,029 | 0.98 | 97 | <3 | 100/101 |
| COMPARATIVE EXAMPLE C | 10,000/6,000 | 1.67 | <3 | 7A | 1,000/1,010 | 0.99 | 98 | <3 | 99/101 |
| 13 | 7,000/6,050 | 1.15 | <4 | 4B | 2,400/1,560 | 1.54 | 102 | 6 | 100/101 |
| 14 | 8,250/6,570 | 1.26 | <3 | 7A | 1,800/1,420 | 1.27 | 100 | 4 | 100/101 |
| 15 | 18,000/7,800 | 2.31 | 16 | 6B | 2,000/1,448 | 1.38 | 101 | 5 | 97/100 |
| 16 | 19,500/8,925 | 2.18 | 7 | 6A | 1,400/1,240 | 1.13 | 101 | 4 | 99/100 |
| 17 | 14,700/7,700 | 1.91 | 24 | 6B | 2,000/1,400 | 1.43 | 103 | 5 | 100/101 |
| 18 | 22,000/9,500 | 2.32 | 40 | 7A | 1,720/1,152 | 1.49 | 101 | 4 | 101/101 |
| 19 | 22,000/8,640 | 2.55 | 30 | 7A | 1,250/1,204 | 1.04 | 100 | 4 | 102/103 |
| 20 | 26,000/9,360 | 2.78 | <60 | 7A | 1,000/1,010 | 0.99 | 99 | 3 | 101/101 |
| 21 | 6,400/4,400 | 1.45 | <3 | 5C | 1,800/1,340 | 1.34 | 97 | 4 | 99/100 |
| 22 | 19,000/9,600 | 1.98 | 16 | 5B | 3,200/1,746 | 1.83 | 104 | 5 | 99/102 |
| 23 | 15,000/8,460 | 1.77 | <4 | 6A | 2,080/1,456 | 1.43 | 102 | 5 | 100/101 |
| 24 | 13,300/7,875 | 1.69 | <3 | 6B | 1,480/1,240 | 1.19 | 99 | 5 | 99/99 |
| COMPARATIVE EXAMPLE D | 16,700/8,100 | 2.06 | 24 | 7A | 1,016/960 | 1.06 | 94 | 3 | 100/101 |
| COMPARATIVE EXAMPLE E | 16,000/9,200 | 1.74 | 16 | 7A | 1,200/1,200 | 1 | 97 | 3 | 101/102 |
| COMPARATIVE EXAMPLE F | 21,400/8,540 | 2.51 | 14 | 6A | 1,080/1,050 | 1.03 | 99 | 4 | 100/100 |
| 25 | 8,400/5,800 | 1.45 | <3 | 3B | 1,400/1,240 | 1.13 | 99 | 4 | 101/99 |
| 26 | 24,400/9,800 | 2.49 | 30 | 7A | 1,200/1,120 | 1.07 | 98 | 3 | 101/100 |
| 27 | 26,000/10,800 | 2.41 | 30 | 7A | 1,200/1,160 | 1.03 | 97 | <3 | 99/101 |
| 28 | 30,800/12,200 | 2.52 | 12 | 7A | 1,200/1,180 | 1.02 | 100 | <3 | 100/101 |
| 29 | 23,400/9,900 | 2.36 | 30 | 7A | 1,300/1,180 | 1.1 | 100 | 3 | 103/100 |
| 30 | 24,000/3,800 | 2.73 | 35 | 7A | 1,200/1,220 | 0.98 | 98 | <3 | 100/101 |
| 31 | 22,000/9,400 | 2.34 | 30 | 7B | 1,240/1,220 | 1.02 | 102 | 3 | 102/100 |
| 32 | 28,000/11,000 | 2.55 | 35 | 7B | 1,400/1,300 | 1.07 | 102 | 3 | 100/101 |
| 33 | 26,000/11,000 | 2.36 | 25 | 7A | 1,300/1,180 | 1.1 | 99 | 3 | 101/100 |
| 34 | 13,000/7,300 | 1.78 | 20 | 7A | 1,400/1,260 | 1.11 | 98 | 3 | 103/101 |
| COMPARATIVE EXAMPLE H | Not tested - solid | | | | | | | | |
| COMPARATIVE EXAMPLE I | 9,200/7,300 | 1.26 | 5 | 7A | 1,200/1,200 | 1 | 97 | <3 | 100/101 |
| COMPARATIVE EXAMPLE J | Not tested - solid | | | | | | | | |
| COMPARATIVE EXAMPLE K | 15,600/7,840 | 1.99 | 20 | 4C | 1,520/1,320 | 1.15 | 99 | 3 | 94/98 |
| 35 | 6,400/5,600 | 1.14 | <3 | 6B | 1,330/1,240 | 1.05 | 100 | 4 | 102/102 |
| 36 | 16,000/8,600 | 1.86 | 14 | 5B | 1,500/1,296 | 1.16 | 100 | 4 | 100/100 |
| 37 | 14,400/8,400 | 1.71 | <3 | 5C | 1,350/1,270 | 1.06 | 101 | 4 | 100/101 |
| 38 | 16,000/9,000 | 1.78 | 3 | 5C | 1,300/1,250 | 1.04 | 99 | 4 | 99/98 |
| 39 | 16,000/9,200 | 1.74 | <3 | 6C | 1,300/1,250 | 1.04 | 100 | 4 | 101/100 |
| 40 | 16,000/8,400 | 1.9 | 8 | 6B | 1,400/1,360 | 1.03 | 103 | 3 | 100/101 |
| 41 | 30,000/11,200 | 2.68 | >60 | 7A | 1,100/1,120 | 0.98 | 101 | 4 | 102/102 |
| 42 | 10,000/6,800 | 1.47 | 4 | 4B | 1,640/1,420 | 1.15 | 103 | 3 | 103/102 |
| 43 | 8,000/6,240 | 1.28 | 4 | 6A | 1,600/1,360 | 1.18 | 103 | 3 | 101/102 |
| 44 | 16,000/8,600 | 1.86 | 8 | 5B | 1,400/1,320 | 1.06 | 101 | 3 | 102/102 |
| 45 | 10,000/7,400 | 1.35 | 4 | 5B | 1,400/1,280 | 1.09 | 104 | 3 | 102/101 |
| 46 | 10,000/8,000 | 1.25 | >3 | 7A | 1,300/1,260 | 1.03 | 103 | 4 | 100/101 |
| COMPARATIVE EXAMPLE L | 12,000/6,600 | 1.82 | 12 | 4C | 1,400/1,220 | 1.15 | 97 | 4 | 100/102 |
| COMPARATIVE EXAMPLE M | 21,200/9,200 | 2.3 | 8 | 7A | 1,000/940 | 1.06 | 94 | 3 | 103/103 |

TABLE 16-continued

Results in a 0.6 (lbs/gal) VOC Epoxy-Polyamide two component system
Loading: 5 pphg

| | BASE PAINT | | | | CURED PAINT | | | | |
|---|---|---|---|---|---|---|---|---|---|
| Example | Brookfield Viscosity, cP 10 RPM/100 RPM | TI | Leneta Sag (mil) | Hegman Grind | Brookfield Viscosity, cP 10/100 RPM | TI | Stormer [KU] | Leneta Sag (mil) | Gloss 20°/60° |
| COMPARATIVE EXAMPLE N | 6000/5,600 | 1.07 | 3 | 7A | 840/860 | 0.98 | 91 | 3 | 101/102 |
| COMPARATIVE EXAMPLE 4 | 4,000/4000 | 1 | <3 | 7A | 1,040/1,016 | 1.03 | 96 | <3 | 98/99 |

TABLE 17

Results in a 0.6 (lbs/gal) VOC Epoxy-Polyamide two component system
Loading: 5 pphg

| | BASE PAINT | | | CURED PAINT | | | | |
|---|---|---|---|---|---|---|---|---|
| Example | Brookfield Viscosity, cP 10 RPM/100 RPM | TI | Hegman Grind | Brookfield Viscosity, cP 10/100 RPM | TI | Stormer [KU] | Leneta Sag (mil) | Gloss 20°/60° |
| 47 | 69,000/19,600 | 3.52 | 6.5C | 5,120/2376 | 2.15 | 108 | 12 | 96/100 |
| 48 | 50,000/18,400 | 2.72 | 6.75B | 5,200/2,320 | 2.24 | 105 | 8 | 99/100 |
| 49 | 66,400/21,360 | 3.11 | 6.75A | 5,360/2,460 | 2.18 | 110 | 14 | 96/100 |
| 50 | 50,000/17,600 | 2.84 | 6.5A-B | 6,000/2,756 | 2.18 | 108 | 10 | 91/100 |
| 51 | 54,000/18,000 | 3.0 | 6.5A-B | 5,720/2,732 | 2.09 | 109 | 10 | 93/100 |
| 52 | 54,000/17,800 | 3.03 | 6.5C | 5,720/2,732 | 2.09 | 109 | 10 | 98/100 |
| 53 | 42,000/15,000 | 2.8 | 6.5B | 4,400/2,440 | 1.8 | 110 | 8 | 97/100 |
| 54 | 52,000/18,000 | 2.89 | 6.5B | 5,800/2,740 | 2.11 | 114 | 8 | 96/100 |
| 55 | 69,000/20,640 | 2.81 | 6.5C | 8,200/3,200 | 2.56 | 112 | 14 | |
| 56 | 42,250/19,200 | 2.2 | 6.75 | 5,750/2,400 | 2.4 | 96 | 10 | 84/95 |
| 57 | 40,000/16,200 | 2.47 | 6.75B | 7,250/2,775 | 2.61 | 106 | 13 | 93/98 |
| 58 | 44,000/11,600 | 3.79 | 6.75 | 9,000/2,900 | 3.10 | 109 | 14 | 95/97 |

The following examples use tris(hydroxymethylamino)methane—Examples 59 to 61.

The general procedure outlined in Example 1 was used, except the reactants were replaced as indicated in Table 18. All examples were liquids.

TABLE 18

| Example | Regents | Parts by wt. | Acid Value* | Amine Value* |
|---|---|---|---|---|
| 59 | Empol 1075 | 32.06 | | |
| | Empol 1004 | 51.03 | | |
| | Tris (hydroxymethyl-amino)methane | 7.27 | 1.0 | 2.9 |
| | Polyethylene glycol (mol.wt. 600) | 36.0 | | |
| | Empol 1004 | 51.03 | | |
| | Tris (hydroxymethyl-amino)methane | 7.27 | 2.3 | 1.0 |
| 61 | Polypropylene glycol (mol.wt. 725) | 43.5 | | |
| | Empol 1004 | 51.03 | | |
| | Tris (hydroxymethyl-amino)methane | 7.27 | 3.7 | 2.9 |

*The acid and the amine values indicated are for the final product.

The above materials were evaluated as described above and the results reported in Table 19.

TABLE 19

| | BASE PAINT | | | | CURED PAINT | | | | |
|---|---|---|---|---|---|---|---|---|---|
| Example | Brookfield Viscosity, cP 10 RPM/100 RPM | TI | Leneta Sag (mil) | Hegman Grind | Brookfield Viscosity, cP 10 RPM/100 RPM | TI | Stormer [KU] | Leneta Sag (mil) | Gloss 60° |
| 59 | 78,000/19,840 | 3.63 | 30 | 3C | 4,800/2,300 | 2.09 | 110 | 8 | 104 |
| 60 | 80,000/19,320 | 4.14 | >60 | 7A-B | 2,480/1,560 | 1.58 | 106 | 3.6 | 104 |
| 61 | 88,000/20,320 | 4.33 | >60 | 6B-C | 6,440/2,852 | 2.26 | 8.6 | 8.6 | 104 |

As can be seen from the data set forth above, the liquid rheological additives of the present invention are effective paint additives yielding excellent viscosity results compared to the several comparative examples in organic systems.

The invention being thus described, it will be obvious that the same may be varied in many ways and in a variety of obvious modifications. Such variations are not to be regarded as a departure from the spirit and scope of the invention and are intended to be covered by its spirit.

What I claim:

1. A liquid rheological additive for organic systems which when free of diluent is pourable at ambient temperature which imparts thixotropy to such systems, comprising the reaction product of:
   a) One or more active hydrogen compounds, wherein the active hydrogen compound contains at least two active hydrogen moieties; and
   b) One or more compounds containing at least two moieties which are capable of reacting with the active hydrogen moieties of (a); and after the reaction of compounds a) and b) is complete, reacting
   c) one or more compounds different than the compounds of a) and b) containing at least three moieties at least one moiety of which is capable of reacting with the reaction product of (a) and (b).

2. The additive of claim 1 wherein the reaction product comprises:
   a) from about 10 to 90 parts by weight of compound a);
   b) from about 2 to 97 parts by weight of compound b); and
   c) from about 1 to 40 parts by weight of compound c).

3. The additive of claim 1 wherein compound b) is one or more polycarboxylic acids.

4. The additive of claim 3 wherein one or more of the polycarboxylic acids is selected from the group consisting of dimer acids and trimer acids.

5. The additive of claim 1 wherein compound c) is selected from the group consisting of aliphatic, cycloaliphatic and aromatic amino alcohols.

6. The additive of claim 5 wherein compound c) is branched.

7. The additive of claim 1 wherein compound c) is 2-amino-2-ethyl-1,3-propanediol.

8. The additive of claim 1 wherein compound c) is a mixture of two or more different compounds.

9. The additive of claim 1 wherein the organic system is selected from the group consisting of paints, coatings, inks, epoxies and polyesters.

10. A liquid rheological additive for organic systems which when free of diluent is pourable at ambient temperature which imparts effective thixotropy to such systems comprising the reaction product of:
    a) one or more polyol compounds;
    b) one or more polycarboxylic acids; and
    c) a compound selected from the group consisting of 2-amino-2-ethyl-1,3-propanediol and tris (hydroxymethyl) aminomethane.

11. The additive of claim 10 wherein compound c) comprises from about 10 to 15 parts by weight of the reaction product.

12. The additive of claim 10 wherein the reaction product contains hydroxyl moieties on its termini.

13. The additive of claim 1 dissolved in a diluent.

* * * * *